(12) United States Patent
George et al.

(10) Patent No.: US 6,627,676 B1
(45) Date of Patent: Sep. 30, 2003

(54) ANTIMICROBIAL BIOCIDIC FIBER-PLASTIC COMPOSITE AND METHOD OF MAKING SAME

(76) Inventors: Richard George, 407 Rockland Ave., Manchester, NH (US) 03102; Mildred A. Saide, 407 Rockland Ave., Manchester, NH (US) 03102; Joseph G. Saide, 3756 Cypress Lake Dr., Lakewood, FL (US) 33467

(*) Notice: Subject to any disclaimer, the term of this patent is extended or adjusted under 35 U.S.C. 154(b) by 0 days.

(21) Appl. No.: 09/648,024

(22) Filed: Aug. 25, 2000

Related U.S. Application Data
(60) Provisional application No. 60/151,102, filed on Aug. 27, 1999.

(51) Int. Cl.$^7$ ................................................. C08L 1/02
(52) U.S. Cl. ........................... 523/122; 524/13; 524/14; 524/35; 524/72
(58) Field of Search .................... 106/16, 15.05, 106/162.5; 442/123, 153; 523/122; 521/40; 524/9, 13, 14, 35, 72; 8/120

(56) References Cited

U.S. PATENT DOCUMENTS

| | | | | |
|---|---|---|---|---|
| 3,350,265 A | * | 10/1967 | Rubenstein et al. | |
| 3,652,496 A | * | 3/1972 | Stapfer | |
| 3,864,468 A | | 2/1975 | Hyman et al. | 424/16 |
| 3,905,926 A | | 9/1975 | D'Alelio | |
| 3,926,644 A | * | 12/1975 | Kaye | |
| 3,932,209 A | * | 1/1976 | Chatterjee | |
| 3,966,659 A | * | 6/1976 | Oxé et al. | |
| 4,086,297 A | | 4/1978 | Rei et al. | 260/859 |
| 4,624,679 A | | 11/1986 | McEntee | 8/650 |
| 4,649,113 A | * | 3/1987 | Gould | |
| 4,663,077 A | | 5/1987 | Rei et al. | 252/364 |
| 4,666,706 A | | 5/1987 | Farquharson et al. | 424/408 |
| 4,666,956 A | | 5/1987 | Spielau et al. | 523/122 |
| 4,686,239 A | | 8/1987 | Rei | 521/55 |
| 4,747,902 A | | 5/1988 | Saitoh | 156/244.11 |
| 4,789,692 A | | 12/1988 | Rei et al. | 523/122 |
| 4,847,088 A | * | 7/1989 | Blank | |
| 4,876,070 A | | 10/1989 | Tsukahara et al. | 422/122 |
| 4,877,617 A | * | 10/1989 | Namikoshi et al. | |
| 4,888,175 A | | 12/1989 | Burton, Jr. et al. | 424/409 |
| 4,891,391 A | | 1/1990 | McEntee | 523/122 |
| 4,918,167 A | * | 4/1990 | Glasser et al. | |
| 4,966,650 A | * | 10/1990 | DeLong et al. | |
| 4,997,488 A | * | 3/1991 | Gould et al. | |
| 5,023,097 A | | 6/1991 | Tyson | 426/271 |
| 5,063,706 A | | 11/1991 | Aki et al. | 43/125 |
| 5,098,417 A | * | 3/1992 | Yamazaki et al. | |
| 5,196,460 A | * | 3/1993 | Lora et al. | |
| 5,288,772 A | | 2/1994 | Hon | |
| 5,505,264 A | * | 4/1996 | Morris et al. | 168/12 |
| 5,554,373 A | | 9/1996 | Seabrook et al. | 424/400 |
| 5,656,037 A | * | 8/1997 | Vigo et al. | |
| 5,700,742 A | * | 12/1997 | Payne | |
| 5,705,216 A | * | 1/1998 | Tyson | |
| 5,856,248 A | * | 1/1999 | Weinberg | |
| 5,882,564 A | * | 3/1999 | Puppin | 524/35 |
| 5,973,035 A | * | 10/1999 | Medoff et al. | |
| 6,200,682 B1 | * | 3/2001 | Dubelsten et al. | 524/35 |

FOREIGN PATENT DOCUMENTS

| | | | | |
|---|---|---|---|---|
| EP | 0144726 | 5/1989 | | 25/2 |
| GB | 1169288 | 11/1969 | | |

OTHER PUBLICATIONS

Lignin Institute, "Lignins—Products With Many Uses," (Winter 1992).
Lignin Institute, "Lignin as a Binder,".
Lignin Institute, "Lignins: Co-Reactant in Adhesive Systems," vol. 5 (No. 1), (Mar. 12, 1996).

* cited by examiner

Primary Examiner—Peter Szekely
(74) Attorney, Agent, or Firm—Devine, Millimet & Branch; Kevin J. Carroll

(57) ABSTRACT

An antimicrobial biocidic fiber-plastic composite is capable of killing bacteria on contact. The composite can be produced from a cellulose fiber material obtained from agricultural waste, a plastic material obtained from industrial waste, and one or more biocides that kill bacteria without being harmful to humans. Lignin is removed from the fiber material through a delignification process to allow the biocides to bind directly with the cellulose fibers. In one example, the biocides include Sodium Hypochlorite, N-chloro-p-toluenesulfonamide sodium salt-trihydrate, Vitamin E and Citric Acid. After adding the biocides, lignin is added back to the mixture to allow the cellulose fibers to bind with the plastic material. The fiber-plastic composition can then be extruded, pelletized, and molded into any shape or size.

31 Claims, No Drawings

ANTIMICROBIAL BIOCIDIC FIBER-PLASTIC COMPOSITE AND METHOD OF MAKING SAME

CROSS-REFERENCE TO RELATED APPLICATIONS

This application claims the benefit of U.S. Provisional Application Serial No. 60/151,102 filed Aug. 27, 1999, fully incorporated herein by reference.

FIELD OF THE INVENTION

The present invention relates to biocidic materials and to fiber-plastic composite materials and more particularly, to the production of an antimicrobial biocidic fiber-plastic composite.

BACKGROUND OF THE INVENTION

Plastic composites, such as fiber-plastic composites, have become increasingly popular because of their variety of applications. In particular, plastic composites made from recycled materials have become popular as a result of environmental concerns.

A plastic composite capable of killing bacteria on contact is also desirable to eliminate health concerns. In some applications, such as food applications, contamination by microorganisms must be avoided. Microbial contamination of food during packaging and transportation is a serious concern among health professionals. If contamination by the packaging or transportation agents occurs, the effort spent to eliminate pathogenic organisms during processing is wasted. Annually, there are literally thousands of reports of food poisoning that are directly the result of the transportation of the food. Ingestion of these contaminants may cause considerable illness, and in some cases death to the infected person.

Existing plastic treatments to address this problem include bacterial resistant polymers in which the bacteria will not penetrate the polymer itself. This treatment does not use a biocidal that kills bacteria on contact and does not avoid the possibility of contamination through transfer of the organism. Prior attempts to use biocidals within polymers have involved treating plastics with chemicals which have been shown to be harmful to humans.

Accordingly, there is a need for a plastic composite that is capable of killing bacteria on contact without being harmful to humans.

SUMMARY OF THE INVENTION

One aspect of the present invention is a method of producing a biocidic fiber-plastic composition. The method comprises obtaining a cellulose fiber material. At least one biocide is mixed with the fiber material such that the biocide binds with the fiber material to form a biocide fiber substrate. A plastic material is mixed with the biocide fiber substrate to form the biocidic fiber-plastic composition.

This method of producing the biocidic fiber-plastic composition preferably includes the additional steps of delignifying the cellulose fiber material prior to mixing the biocide with the fiber material. Lignin is then added to the biocide fiber substrate prior to mixing with the plastic material.

Another aspect of the present invention is a method of producing a fiber-plastic composition. This method comprises obtaining a fiber material, delignifying the fiber material to form a delignified fiber material, and drying the delignified fiber material. At least one chemical is then added to the delignified fiber material to chemically treat the fiber material. Lignin is then added to the delignified fiber material, and the fiber and lignin are mixed with a plastic material. One example of the chemical added to the delignified fiber material is at least one biocide.

Another aspect of the present invention is a method of producing a biocidic fiber material. According to this method, a cellulose fiber material is mixed with at least one biocide. The biocide replaces hydroxyl groups at the end of the cellulose molecule with chlorine.

A further aspect of the present invention is a product made according to any one of the methods defined above.

Yet another aspect of the present invention is a biocidic fiber-plastic composition comprising a fiber material, at least one biocide bound to the fiber material, and a plastic material bound to the fiber material.

The biocide used in the above methods and products preferably includes at least one biocide capable of replacing hydroxyl groups at the end of the cellulose molecule with chlorine. In one example, the biocide includes one or more of the following: Sodium Hypochlorite, N-chloro-p-toluenesulfonamide sodium salttrihydrate, and Vitamin E. The fiber material can be obtained from recycled agricultural waste. The plastic material can be obtained from recycled industrial waste.

DETAILED DESCRIPTION OF THE PREFERRED EMBODIMENTS

The antimicrobial biocidic fiber-plastic composite, according to the present invention, includes a fiber material, a plastic material, and at least one antimicrobial biocide. In general, the fiber-plastic composite is produced by combining the antimicrobial biocide with the fiber material such that the antimicrobial biocide binds with the cellulose fiber to form a biocide fiber substrate. The biocide fiber substrate is mixed with a plastic material to form a fiber-plastic composition. The fiber-plastic composition can then be formed into the antimicrobial biocidic fiber-plastic composite having any desired shape or configuration.

According to one preferred method, cellulose fiber material is first obtained from agricultural waste. Any cellulose containing plant (bagasse, corn, wheat, hay, pineapple, and the like) can be used for this invention. Alternatively, a pure cellulose can be used instead of recycling agricultural waste.

The fiber material is delignified, for example, using a reagent or by adding the reagent in addition to steam explosion. In one example, the fiber material is delignified using a combination of a 50% solution of Potassium Hydroxide and a 50% solution of Sodium Hydroxide, which is mixed into the fiber for at least about 15 minutes. Alternatively, a weak caustic soda for a minimum period of 30 minutes may also be used. Depending on the type of agricultural waste utilized, its density, and the permeability of the fiber, between 8 and 400 ppm of any of the bases described above are used. In order to mix well, the moisture content of the agricultural waste at the time the base is added is preferably a minimum of about 25%.

Steam explosion is preferably utilized after the fiber-base combination has been mixed thoroughly. The steam explosion process is accomplished through steam and pressure and is generally known to one of ordinary skill in the art. The temperature at the time of the explosion is preferably a minimum of about 72 degrees C.

The fiber is then placed in a dryer and dried to below about a 2% moisture content. The physical structure (i.e., all dimensions) of the dried fibers should preferably not be greater than about 0.8 cm, otherwise there may be difficulty binding. Using this chemical and thermo-degregation delignification process, the cellulose fiber is isolated and recovered from the agricultural waste. Once the cellulose is recovered, it can be treated chemically to allow combining with various recycled and/or virgin plastic polymers to form a wood-like material for many uses, as described in greater detail below.

Other delignification processes can also be used. One such delignification process uses extrusion technology as described in detail in U.S. Pat. No. 5,023,097, incorporated herein by reference. Alternatively, a delignified cellulose fiber material can be obtained and used as the starting material (i.e., instead of using agricultural waste). Also, this method can include additional steps of chemically treating the fiber material to remove impurities (in addition to removing the lignin).

After the delignification process is complete, the delignified cellulose fiber is then placed in a mixing/storage tank and one or more antimicrobial biocides are added. The antimicrobial biocides preferably eliminate microbial contamination by killing certain types of bacteria on contact. The biocides used in the present invention preferably bind with the cellulose without interfering with the bonding with plastic. Thus, at least one biocide is preferably capable of providing chloride replacement at some of the hydroxyl groups.

The antimicrobial agents or biocides used in the present invention are also preferably safe for human contact, safe when used in contact with food items, and derived from natural ingredients or from compositions known to be non-toxic. In the exemplary embodiment, the antimicrobial biocides include, but are not limited to, Sodium Hypochiorite, N-chloro-p-toluenesulfonamide sodium salt-trihydrate, Vitamin E, and citric acid. Citric acid, which is also an effective antimicrobial agent, has been found to facilitate the release of some antimicrobial agents.

Various known biocides or antimicrobial agents other than those mentioned above can also be used. The delignified cellulose can also be used to link with other chemicals, thereby creating a means of combining with plastic or to form other chemical bonding when mixed with plastic.

In the exemplary preferred method, Sodium Hypochlorite is added to the delignified fiber substrate at between about 20 and 2,000 ppm concentration. When the Sodium Hypochlorite is added, choride replacement occurs such that some of the hydroxyl groups at the end of the cellulose molecule are replaced with chlorine. This enables the destruction of specific microbial growths.

Vitamin E is then added for greater antimicrobial protection. The Vitamin E is usually added as a liquid at about 400 to 500 cc per ton of agricultural waste. Greater amounts have not shown to provide additional protection, however, no degradation has been found to occur.

Citric acid or a low grade hydrochloric acid is then added. Citric acid extract facilitates the release of the biocidal ingredient from an antimicrobial composition. Citric acid extract is obtained from a variety of sources, any particular form of which can be used in the present invention. One of the particular classes of compounds whose release is facilitated by citric acid extract according to the present invention is N-chloro-p-toluenesulfonamide sodium salt-trihydrate. The selection of this compound was made as a result of it being approved by the Environmental Protection Agency (EPA) for use on food-contact surfaces.

Since N-chloro-p-toluenesulfonamide sodium salt-trihydrate does not migrate well when extruded into a fiber-plastic compound, the addition of citric acid to the polymeric composition is required to facilitate the release of N-chloro-p-toluenesulfonamide sodium salt-trihydrate from the newly formed fiber-plastic compound. The citric acid is used like an enzyme and breaks down the trihydrate without reacting with it.

The density of the agricultural waste plus the permeability of the waste determines the amounts of citric acid and N-chloro-p-toluenesulfonamide sodium salt-trihydrate. Citric acid is preferably added in the amount of approximately 340 cc per ton of agricultural waste but no greater than about 600 cc. Any amount greater than 600 cc has been shown to cause degredation of the cellulose. As a result, the acetal linkages are attacked, resulting in the cleaving of the 1-4-glycosidic bonds. Once this occurs, concurrent reactions occur which reduce the biocidal effects of the antimicrobial agents.

N-chloro-p-toluenesulfonamide sodium salt-trihydrate is then added at about 5 times the amount of the citric acid. This composition allows for the best migration of the trihydrate. Although the biocides described above are added separately in the exemplary embodiment, this is not a limitation of the present invention.

The resulting composition of Sodium Hypochlorite, N-chloro-p-toluenesulfonamide sodium salt-trihydrate, Vitamin E and Citric Acid will destroy or inhibit the growth of various bacteria, viruses, and fungi. This is particularly important since, in many applications, the object that is to be protected from microbial infestation is subject to attack from more than one variety and species of microorganisms. Examples of the types of bacteria or microorganisms that can be killed by the present invention include, but are not limited to:

*Escherichia coli* 0157:H7
Fungi
*Aspergillus flavus*
*A. fumigalus*
*A. niger*
*Blastomyces dermatitidis*
Candida spp.
*Coccidioides immitis*
*Cryptococcus neoformans*
*Fusarium culmorum*
*Histoplasma capsulatum.*
Microsporum spp.
*Mucor racemosus*
Nocardia spp.
Penicillium spp.
*Rhizopus higricans*
*Saccharomyces cerevisiae*
Trichophyton spp.
*Aerobacter aerongenes*
*Aeromonas hydrophila*
*Bacillus cereus*
*Bacillus subtilis*
*Bordetella pertussis*
*Borrelia burgdorferi*
*Lactobacillus acidophilus*
*Corynebacterium diphtheriae*
*C. bovis*

*Desulfovibrio desulfurica*
Enteropathogenic *E. coli*
Enterotoxin-producing *E. coli*
*Helicobacter pylori*
*Leptospira interrogans*
*M. bovis*
*Proteus mirabilis*
*P. vulgaris*
*Pseudomonas aeruginosa*
*Rhodococcus equi*
*Salmonella choleraesuis*
*S. enteridis*
*S. typhimurlum*
*S. typhosa*
*Staphylococcus aureus*
*S. epidermidis*
*Streptococcus anginosus*
*S. mutans*
Actinomycetes
*Stretomyces reubrireticuli*
*Streptoverticillium reticulum*
*Thermoactinomyces vulgaris*
Coronaviruses
Enteroviruses
Herpes simplex virus
Morbillivirus
Norwalk viruses
Papillomaviruses
Paromyxovirus
Respiratory Synctial virus
Rhinoviruses After the biocides are added to the delignified cellulose fiber, lignin is then added back to the biocide fiber substrate so that the fiber can be combined with plastic. The treatment of the pure cellulose with Lignin forms a cellulose/lignin mixture. Once Lignin is separated from other plant components, it can be chemically modified to allow the recombination with cellulose and act as a binding agent when combined with plastic. Various types of lignin have been used and all found to be effective in the mixture with cellulose. This includes Kraft lignin, coniferous lignins, solvolysis lignin, lignin extracted by acid hydrolysis, lignin extracted through various fractionations, as well as lignin extracted though dissolving agricultural products in water.

The biocidic fiber and lignin are then mixed with the plastic material, which is obtained, for example, from industrial waste. According to the exemplary embodiment, the mixture includes about 10% to 60% of the biocidic fiber and lignin. The plastic material can be numerous virgin or recycled plastic resins including, but not limited to, polyethylenes, polypropylenes, polystyrenes, polyacrylates, polyvinylchlorides, polyurethanes. The choice of the polymer used depends mostly upon the application. For example, polyethylene or polyvinylchloride are preferably used in plastic sheeting because of its flexibility and physical characteristics.

The biocidic fiber-plastic mixture is then extruded, for example, into pellets. The extrusion temperature can vary from about 68 degrees C to 230 degrees C depending on the composite produced. The extrusion process is accomplished by extrusion, i.e. forcing heated, fiber-plastic composite continuously through a die. This die has an opening shaped to produced the desire finished pellet.

The extruder preferably has a modified screw that allows for constant mixing during extrusion. The distance between each element of the screw preferably varies from about 0.6 cm. to 4 cm. apart. In addition, each element of the screw must be variable in length from its adjacent element. The length of the elements vary, for example, from about 0.4 cm. To 16.5 cm. and are positioned based on the density of the agricultural waste to be used and the speed of the extruder.

After the pellets have been extruded through the die, the extruded material is hardened by cooling. The cooling method utilizes air or water. The pellets can then be further extruded or molded to form various end products. These end products include construction materials, pallets, railroad ties, docks, decks, automotive parts, sheets, lumber, etc.

Another option is to process the fiber and plastic directly for molding without pelletizing. This requires detailed attention to the mixing procedure prior to molding. A twin screw extruder can be used for the extrusion of sheets or boards.

One exemplary use for the antimicrobial biocidic fiber-plastic composite is in the packaging and transportation of food, for example, in pallets used to transport beverage cans. The antimicrobial biocidic fiber-plastic composite can be used in any application where bacterial contamination may be a problem.

One example of a biocide fiber-plastic composite was made according to the exemplary process described above and was tested. The test was performed to determine if the pelletization and molding of the biocidal composition affected the growth inhibiting and destroying properties of the biocidal fibers. In order to ascertain if these properties remained after heat treatment of the fiber-plastic composition, the samples set forth in TABLE 1 were treated with various microorganisms and taken to a medical facility for microorganism testing and identification.

TABLE 1

| Description of Samples | | | |
|---|---|---|---|
| Sample | Color | Size | Description |
| A | light Gray | 1 × 2 × 1 cm. | Pelletized and molded fiber-plastic composite containing biocidal agents according to present invention. |
| B | light Gray | 1 × 2 × 1 cm. | Pelletized and molded fiber-plastic composite without biocidal agent. |
| C | light Gray | 1 × 2 × 1 cm. | Pelletized and molded fiber-plastic composite lightly sprayed on the surface with biocidal agent. |
| D | light Yellow | 1 × 2 × 0.8 cm. | A portion of wood from a wood pallet. |
| E | white/clear | 1 × 2 × 0.1 cm. | A portion of HDPE from a milk jug. |
| F | clear | 1 × 2 × 0.1 cm. | A portion of PET from a soda bottle. |

Each sample was placed in a 100 ml sterilized tube containing 30 ml of thioglycollate broth, mixed for 30 seconds and allowed to settle. 1.0 ml of broth from each test was then put into a petri dish and marked "undiluted" along with the sample identification. Each broth was then diluted to 1:100 and 1:1,000 and the diluted broth was poured into petri dishes marked with the sample identification and amount of dilution. All of the petri dishes were then incubated at 35° C. for 24 hours. The colonies were counted, and the samples were dyed and identified. In some cases, specific broths were further required for additional growth to specifically identify the microorganism.

The following microorganisms were identified following inoculation, incubation, standard aerobic colony count and microscopic analysis:

Staphylococcus aureus
Enteropathogenic E. coli
Cryptococcus neoformans
Fusarium culmorum
Histoplasma capsulatum
Microsporum spp.
Mucor racemosus
Penicillium spp.
Rhizopus higricans
Aerobacter aerongenes
Aeromonas hydrophila
Bacillus cereus
Bacillus subtilis
Bordetella pertussis
Escherichia coli
Helicobacter pylori
Pseudomonas aeruginosa
Salmonella choleraesuis
Shigella sonnei
S. Dysenteriae
Streptococcus anginosus
Actinomycetes
Stretomyces reubrireticuli
Streptoverticillium reticulum
Echinococcus granulosus
Entamoeba coli
E. histolytica

TABLE 2

Test Results

| Sample | Broth with test pieces | Undiluted | 1:100 | 1:1000 | CFU |
| --- | --- | --- | --- | --- | --- |
| A | Clear | 1 | 1 | 0 | <100 |
| B | 3+ | 100 | 1 | 1 | 8,000 |
| C | Clear | 1 | 1 | 1 | <100 |
| D | 4+ | TNTC | TNTC | 40 | 50,000 |
| E | 4+ | TNTC | 300 | 7 | >10,000 |
| F | 4+ | TNTC | 200 | 10 | >10,000 |

In summary, Sample A, which was made according to the present invention, showed no growth of any of the prepared cultures. In addition, Sample C, which was sprayed with the biocide, showed no growth. However, after 3 weeks further testing of Sample C showed some growth of microorganisms.

Accordingly, the present invention provides an antimicrobial biocidic fiber-plastic composite capable of killing bacteria on contact without harming humans. By utilizing a fiber-plastic compound, the biocidal can be applied to the cellulose fiber allowing non-toxic biocides to attach to the cellulose. Using recycled agricultural and industrial waste to produce the antimicrobial biocidic fiber-plastic composite addresses environmental concerns.

Modifications and substitutions by one of ordinary skill in the art are considered to be within the scope of the present invention which is not to be limited except by the claims which follow. For example, the biocidic fiber material can be used in other applications without combining with plastic resins.

What is claimed is:

1. A method of producing a biocidic fiber-plastic composition, said method comprising:
    obtaining a cellulose fiber material;
    mixing at least one biocide with said fiber material, wherein said biocide provides chloride replacement of some hydroxyl groups in cellulose molecules of said cellulose fiber material, thereby binding with said fiber material to form a biocide fiber substrate; and
    mixing a plastic material with said biocide fiber substrate to form said biocidic fiber-plastic composition.

2. The method of claim 1 wherein said fiber material is obtained from recycled agricultural waste.

3. The method of claim 1 further including:
    delignifying said cellulose fiber material prior to mixing said at least one biocidal agent with said fiber material; and
    adding lignin to said biocide fiber substrate prior to mixing said plastic material.

4. The method of claim 3 wherein delignifying includes mixing a combination of approximately a 50% solution of Potassium Hydroxide and a 50% solution of Sodium Hydroxide into said cellulose fiber material.

5. The method of claim 4 wherein said combination is mixed for at least about 15 minutes.

6. The method of claim 4 wherein delignifying further includes mixing a weak caustic soda into said cellulose fiber material.

7. The method of claim 4 wherein delignifying further includes utilizing steam explosion.

8. The method of claim 6 wherein the temperature at the time of said steam explosion is at least about 72° C.

9. The method of claim 1 wherein said at least one biocide includes Sodium Hypochlorite.

10. The method of claim 9 wherein said at least one biocide further includes Vitamin E.

11. The method of claim 10 wherein said at least one biocide further includes N-chloro-p-toluenesulfonamide sodium salt-trihydrate and citric acid.

12. The method of claim 1 wherein said plastic material is obtained from recycled industrial waste.

13. The method of claim 1 wherein said cellulose fiber material is delignified.

14. A biocidic fiber-plastic composition made according to the method of claim 1.

15. A method of producing a fiber-plastic composition, said method comprising:
    obtaining a fiber material;
    delignifying said fiber material to form a delignified fiber material;
    drying said delignified fiber material;
    adding at least one chemical to said delignified fiber material to chemically treat said delignified fiber material;
    adding lignin to said delignified fiber material; and
    mixing a plastic material with said fiber and said lignin, wherein said lignin acts as a binder causing said fiber to bind with said plastic material.

16. The method of claim 15 further including adding at least one biocide to said delignified fiber material prior to adding said lignin.

17. A fiber-plastic composition made according to the method of claim 15.

18. A method of producing a biocidic fiber material, said method comprising:

obtaining a cellulose fiber material; and mixing at least one biocide with said cellulose fiber material, said biocide including Sodium Hypochlorite, wherein said biocide provides chloride replacement of some hydroxyl groups in cellulose molecules of said cellulose fiber material.

19. The method of claim 18 wherein said cellulose fiber material is delignified.

20. The method of claim 18 further including the step of delignifying said fiber material prior to mixing said at least one biocide.

21. The method of claim 20 further including the step of drying said delignified fiber material before mixing said biocide.

22. The method of claim 18 wherein the step of mixing said at least one biocide includes:

mixing said Sodium Hypochlorite with said fiber material;

mixing Vitamin E with said fiber material;

mixing citric acid with said fiber material; and mixing N-chloro-p-toluenesulfonamide sodium salt-trihydrate with said fiber material.

23. The method of claim 22 wherein said Sodium Hypochlorite is added at a concentration between about 20 and 2,000 ppm; said Vitamin E is added at about 400 to 500 cc per ton of fiber material; wherein said citric acid is added at about 340 to 600 cc per ton of fiber material; and wherein said N-chloro-p-toluenesulfonamide sodium salt-trihydrate is added at about 5 times the amount of said citric acid.

24. A biocidic fiber material made according to the method of claim 18.

25. The biocidic fiber material of claim 24 wherein said at least one biocide further includes Vitamin E, citric acid, and N-chloro-p-toluenesulfonamide sodium salt-trihydrate.

26. A biocidic fiber-plastic composition comprising:

a fiber material;

at least one biocide bound to said fiber material, wherein said biocide provides chloride replacement of some hydroxyl groups in cellulose molecules of said fiber material; and a plastic material bound to said fiber material.

27. The biocidic fiber-plastic composition of claim 26 wherein said biocidic fiber-plastic composition is pelletized.

28. The biocidic fiber-plastic composition of claim 26 wherein said biocidic fiber-plasic composition is formed as a sheet.

29. The method of claim 1 further including the step of extruding said biocidic fiber-plastic composition.

30. The method of claim 29 wherein said biocidic fiber-plastic composition is extruded into pellets.

31. The method of claim 29 wherein said biocidic fiber-plastic composition is extruded into a sheet or board.

* * * * *